United States Patent
Uang et al.

[11] Patent Number: 6,127,537
[45] Date of Patent: Oct. 3, 2000

[54] METHOD FOR PREPARING 3-AMINO-1,2-PROPANDIOL DERIVATIVES

[75] Inventors: Biing-Jiun Uang, Taipei; Jia-Wen Chang, Taichung, both of Taiwan

[73] Assignee: Everlight USA, Inc., Pineville, N.C.

[21] Appl. No.: 09/458,003

[22] Filed: Dec. 10, 1999

[51] Int. Cl.[7] ........................ C07C 213/00; C07D 413/04
[52] U.S. Cl. ......................... 544/134; 564/165; 564/349; 564/399
[58] Field of Search ............................ 544/134; 564/165, 564/349

[56] References Cited

U.S. PATENT DOCUMENTS

| | | | |
|---|---|---|---|
| 3,655,663 | 4/1972 | Wasson | 564/349 |
| 4,990,668 | 2/1991 | Mai et al. | 564/349 |

*Primary Examiner*—Robert W. Ramsuer
*Attorney, Agent, or Firm*—Bacon & Thomas

[57] ABSTRACT

A method for the preparation of 3-amino-1,2-propandiol derivatives of the formula (I)

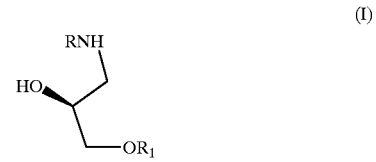

(I)

by reacting a compound of the formula (II)

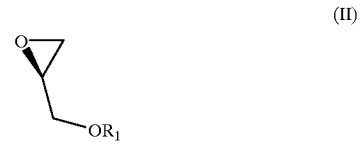

(II)

with $RNH_2$, wherein R and $R_1$ have the same meaning as given in the description. The formula (I) derivatives are β-blockers used for treating hypertension.

6 Claims, No Drawings

METHOD FOR PREPARING 3-AMINO-1,2-PROPANDIOL DERIVATIVES

FIELD OF THE INVENTION

The invention relates to chemical synthetic methods for preparing various 3-amino-1,2-propandiol derivatives, and, more particularly, to the synthetic methods for preparing various β-blockers which are medicines for the treatment of hypertension.

BACKGROUND OF THE INVENTION

A great deal of β-blockers such as (S)-Timolol, (S)-Propranolol, (S)-Atenolol, (S)-Metoprolol,

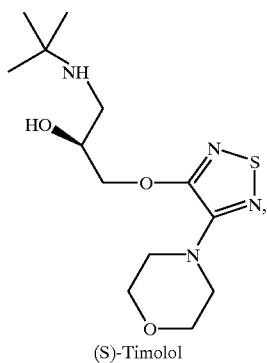

(S)-Timolol

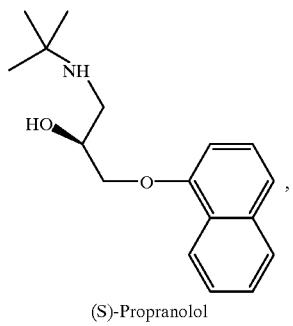

(S)-Propranolol

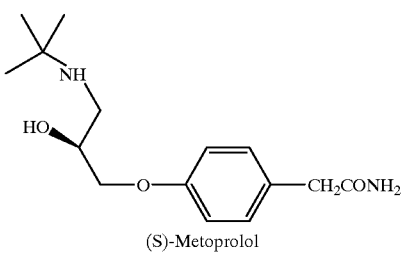

(S)-Metoprolol

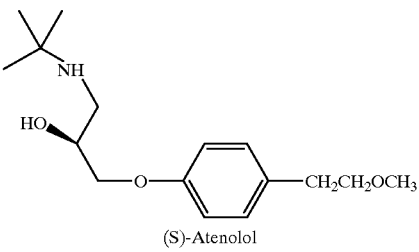

(S)-Atenolol etc. for hypertension patients consist of a primary structure of 3-amino-1,2-propandiol. Those are synthesized in individual processes, such as the synthesis of (S)-Timolol reported by Weinstock, L. M.; Mulvery, D. M.; Tull, R. J. Org. Chem. 1976, 41, 3121. However, when using $PbOAc_4$ during the process in mass production, the pollution causing by products create a waste disposal problem. Another method of synthesizing (S)-Propranolol was reported on Carlsen, P. H. J., Aase, K. Acta. Chem. Scand. 1993, 737.

All of the β-blockers used for hypertension patients have the same primary structure of 3-amino-1,2-propandiol. It would be valuable to develop a common method to produce those different β-blockers through the same synthetic pathway by selecting proper reagents or starting materials.

SUMMARY OF THE INVENTION

The present invention provides a process for the preparation of 3-amino-1,2-propandiol derivatives.

The β-blockers, such as (S)-Timolol, (S)-Propranolol, (S)-Atenolol, (S)-Metoprolol, etc. for hypertension patients can be represented by the derivatives of 3-amino-1,2-propandiol of the following formula (I),

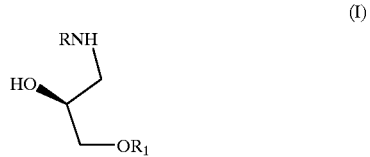

wherein R is $C_{1-4}$ alkyl group,

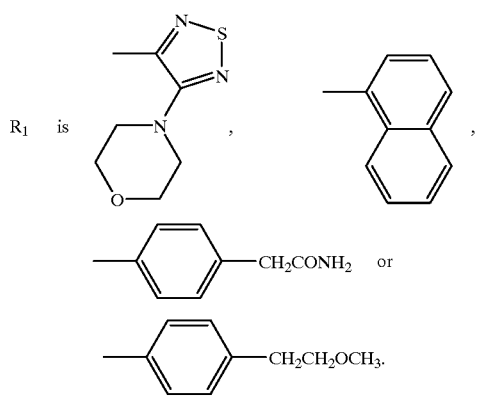

The above β-blockers of formula (I) can be synthesized by using the preparation method provided by the present invention.

The method of the present invention can be described as the following scheme (a).

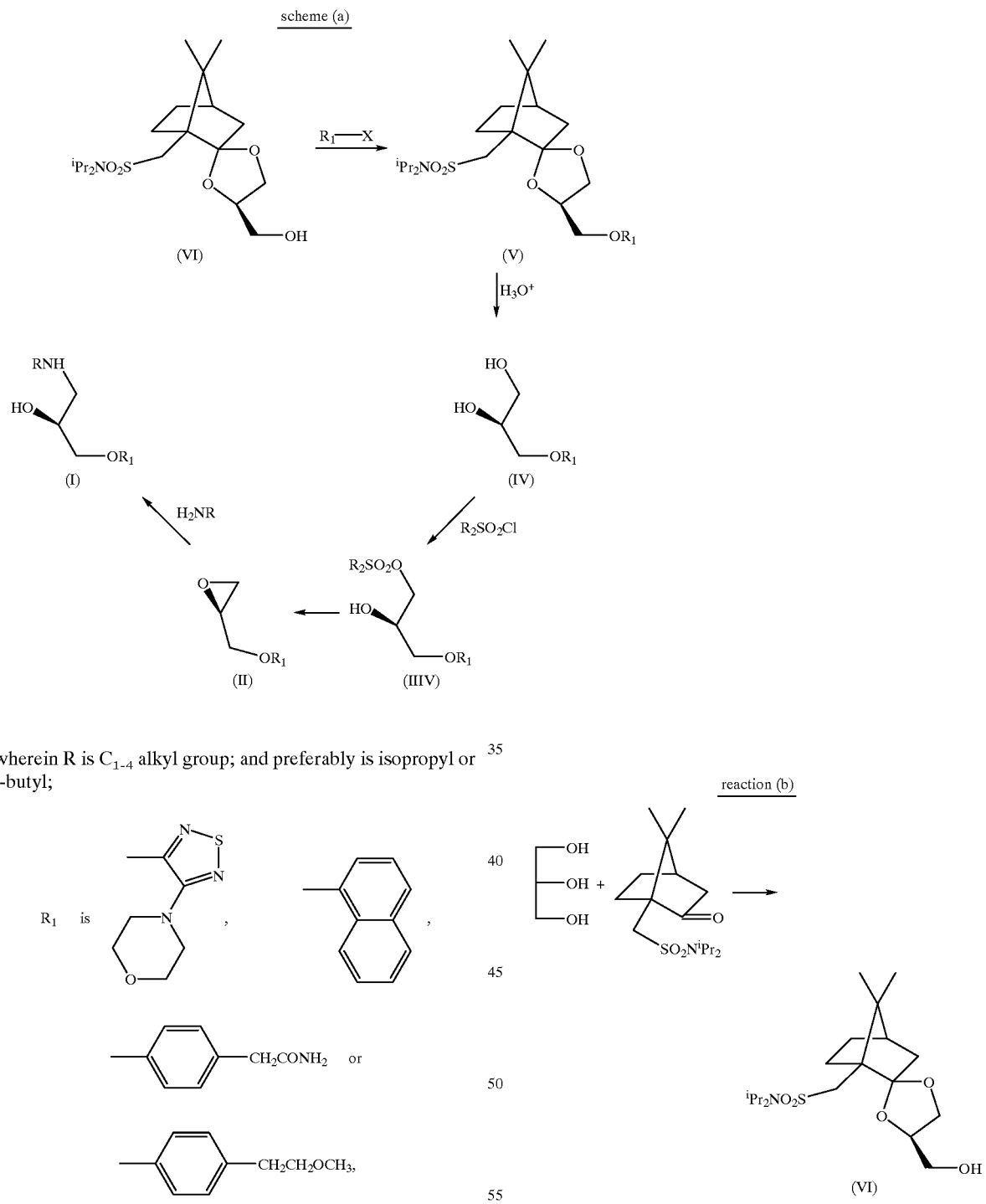

wherein R is $C_{1-4}$ alkyl group; and preferably is isopropyl or t-butyl;

$R_1$ is $R_2$ is a $C_{1-4}$ alkyl group, a phenyl group, a benzyl group, or a phenyl group substituted by $C_{1-4}$ alkyl group or halogen; and preferably is a methyl group, a phenyl group, or a benzyl group; X is halogen.

Hsu, C. Y.; Lin, Y. S.; Uang, B. J. Tetrahedron: Asymmetry 1990, 1,219 reported on the method of synthesizing a formula (VI) compound referred as the following reaction (b)

by using glycerol and chiral auxiliary reagent through an acetalization to obtain the formula (VI) compound.

The present invention first introduces compound (VI), a chiral glycerol equivalent which undergoes a substitution reaction with halogen alkyl $R_1X$ ($R_1$ and X are defined as the above) in the presence of a base such as t-BuOK, $K_2CO_3$, or NaH (preferably NaH) to obtain the formula (V) compound. This substitution reaction is proceeded at the reflux temperature using t-BuOH or DME (dimethoxyethane) as the solvent.

The formula (V) compound is followed by hydrolysis with an acid (such as hydrochloric acid) in methanol to obtain the formula (IV) compound.

The formula (IV) compound is then treated with $R_2SO_2Cl$ ($R_2$ is defined as the above) to become the formula (III) compound.

The formula (III) compound is treated with NaH to undergo an intra-molecule substitution reaction to form the formula (II) compound.

The formula (II) compound undergoes a substitution reaction with $RNH_2$, wherein R is $C_{1-4}$ alkyl group, to form the 3-amino-1,2-propandiol derivatives of formula (I).

Furthermore, the formula (V) compound can also be synthesized by reacting the formula (VI) compound with $R_2SO_2Cl$ to form a formula (VI') compound (as shown in the following scheme (c), wherein $R_1$, $R_2$, and X are defined as the above). The formula (VI') compound is then treated with $R_1OH$ to get the formula (V) compound.

wherein R is $C_{1-4}$ alkyl group;

$R_1$ is

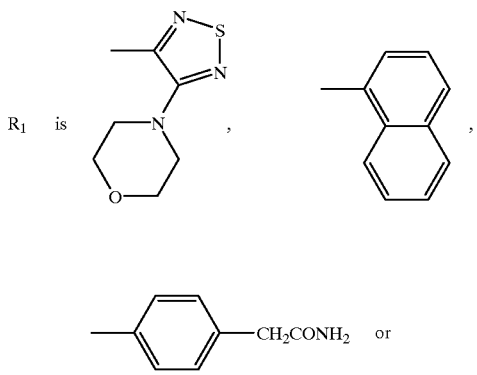

-continued

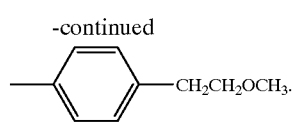

scheme (c)

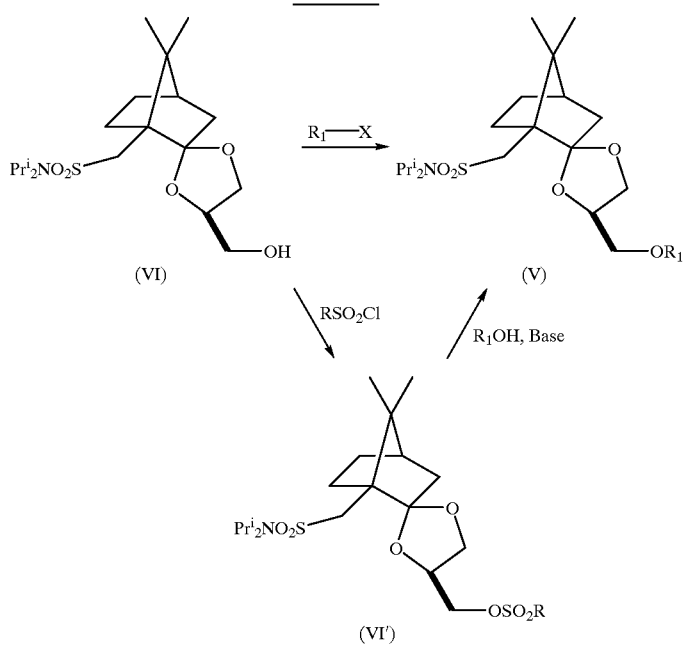

β-blockers such as (S)-Timolol, (S)-Propranolol, (S)-Atenolol, (S)-Metoprolol, etc. for hypertension patients can be easily synthesized by using the method provided by the present invention.

DESCRIPTION OF THE PREFERRED EMBODIMENTS

The present invention relates to synthesizing 3-amino-1,2-propandiol derivatives of the formula (I)

The formula (I) of the present invention can be prepared by reacting a compound of the following formula (II)

(II)

with $RNH_2$ wherein R is $C_{1-4}$ alkyl group, $R_1$ is defined as the above.

The formula (II) compound can be prepared by reacting a compound of the following formula (IV)

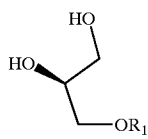

wherein $R_1$ is defined as the above, with $R_2SO_2Cl$, wherein $R_2$ is defined as the above. The product then is treated with NaH.

The formula (IV) compound can be prepared by reacting a compound of the following formula (VI)

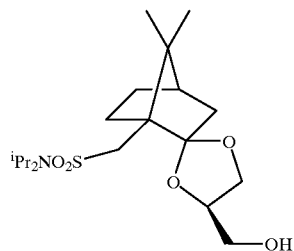

with $R_1X$, wherein $R_1$ is defined as the above and X is halogen(e.g., F, Cl, Br, or I), followed by a hydrolysis reaction. The synthesis of the formula (VI) compound was reported in the reference of Hsu, C. Y., which is incorporated herein by reference.

More detailed examples are used to illustrate the present invention, and these examples are used to explain the present invention. The examples below, which are given simply by way of illustration, must not be taken to limit the scope of the invention.

PREPARATION EXAMPLE 1

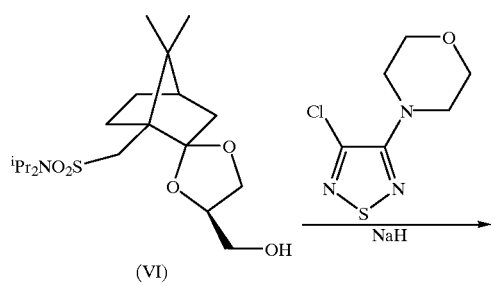

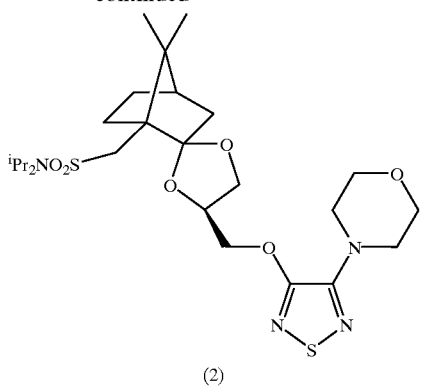

60% NaH (0.267 g) was added into a 50 ml flask and was washed twice with anhydrous n-hexane. After the solvent was removed in vacuum, then anhydrous 1,2-dimethoxyethane (25 ml) was added. The formula (VI) compound (1.99 g) was added at the temperature of 0° C. Then 3-chloro-4-(N-morpholino)-1,2,5-thiadiazole (2.13 g) was added and heated to the reflux temperature. After the reaction was completed, water (10 ml) was added at a temperature of 0° C. The resulting mixture was extracted with ethyl acetate. After separating by chromatography, 2.732 g of a white solid compound of the formula (2) was obtained. M.P.: 131.8~132.6° C., yield: 95%.

PREPARATION EXAMPLE 2

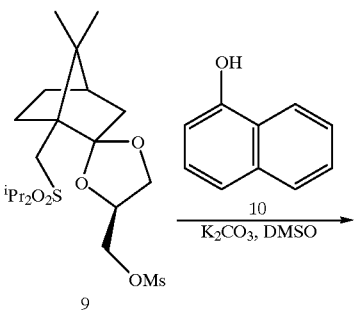

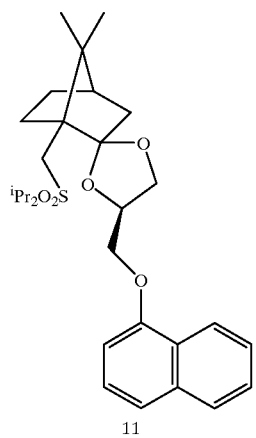

Under anargonatmosphere, the formula (9) compound (2.68 g; 5.8 mmole), $K_2CO_3$ (1.77 g; 12.9 mmole), the formula (10) compound (1.08 g; 7.47 mmole), and anhydrous DMSO (25 ml) were added into a 50 ml flask. The solution was heated to 100° C. for reaction for 22 hours. Then H₂O (20 ml) was added and the resulting solution was extracted with ethyl ether (50 ml×3). The organic layer was washed with brine and was dried with sodium sulfate. After separation by chromatography, 2.01 g (3.9 mmole) of a white solid compound of formula (11) was obtained. M.P. : 170~170.6° C., yield: 68%.

PREPARATION EXAMPLE 3

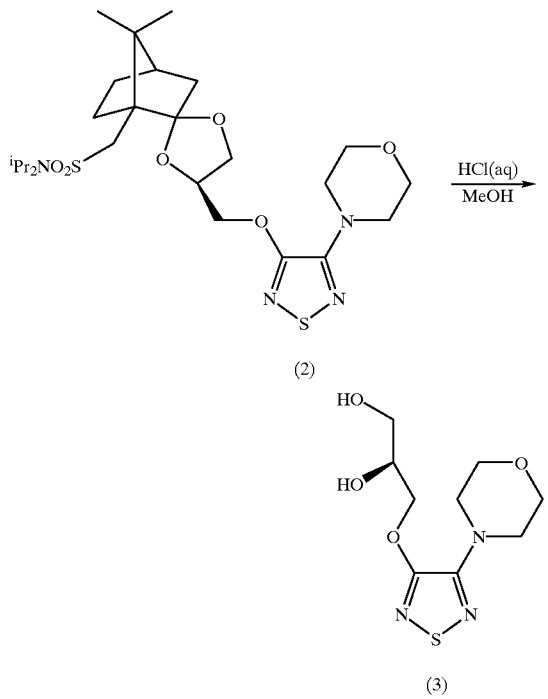

The formula (2) compound (1.53 g), methanol (7 ml), and 2N HCl(aq) (2.8 ml) were added into a 50 ml flask. The solution was heated to 60° C. After the reaction was completed, 3 ml H₂O was added at room temperature. The resultant mixture was neutralized with NaOH to pH 7~8, and was extracted with ethyl acetate. After separating by chromatography, 0.652 g of a white solid compound of formula (3) was obtained. M.P.: 22.8~123.4° C., yield: 91%.

PREPARATION EXAMPLE 4

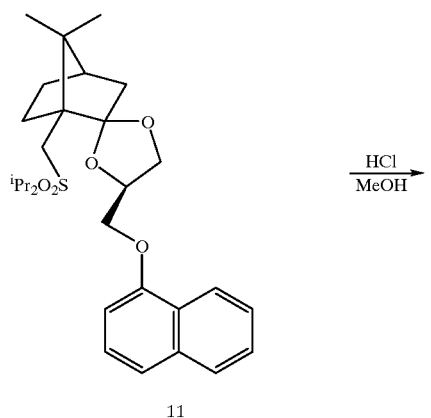

-continued

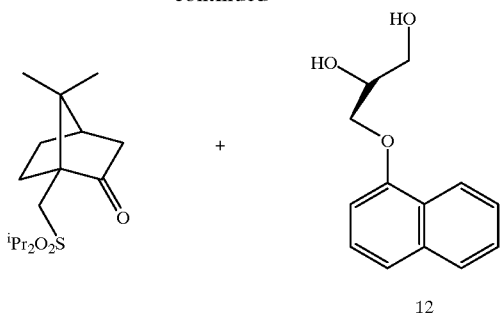

The formula (11) compound (2.01 g; 3.88 mmole), methanol (9 ml), and 2N HCl(aq) (4 ml; 8 mmole) were added into a 25 ml flask. The solution was heated to 70° C. for 10 hours. After the reaction was completed, 10 ml H₂O was added at room temperature. The resultant mixture was neutralized with 1M NaOH(aq) to pH 7~8, and was extracted with ethyl acetate (50 ml×3). The organic layer was washed with brine then dried with anhydrous sodium sulfate. After separation by chromatography, 0.766 g (3.51 mmole) of a white solid compound of formula (12) was obtained. M.P.: 111.2~111.9° C., yield: 95%.

PREPARATION EXAMPLE 5

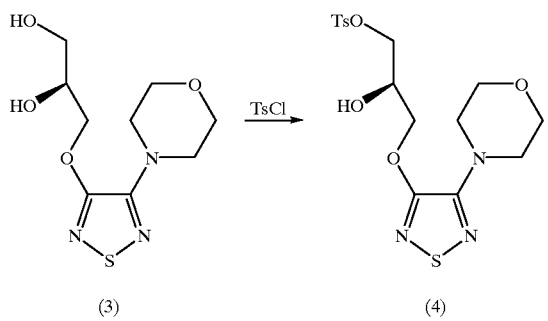

The formula (3) compound (1.5 g), anhydrous dichloromethane and anhydrous pyridine (2.5 ml) were added into a 100 ml flask. Toluene sulfonyl chloride (TsCl; 1.2 g) was added into the solution at −5~−10° C. After the reaction was completed, 20 ml of H₂O was added at room temperature. The resulting mixture was extracted with dichloromethane. After separation by chromatography, 1.61 g of a white solid compound of formula (4) was obtained. yield: 91%.

PREPARATION EXAMPLE 6

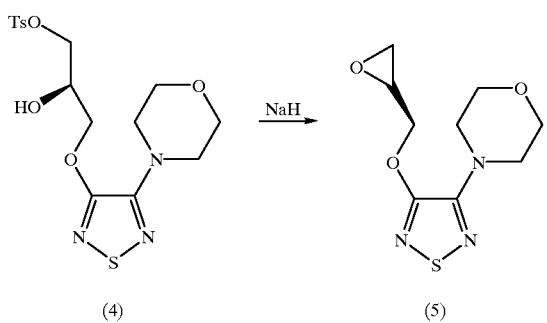

80% NaH (0.22 g) in a 50 ml flask was washed with anhydrous n-hexane (2 ml×2) anhydrous THF (2 ml×1). After solvent was removed in vacuum, then anhydrous THF (12 ml) was added. The formula (4) compound (1.47 g) was added at 0° C. After the reaction was completed, water (10 ml) was added at 0° C. The resulting mixture was extracted with ethyl acetate. After separation by chromatography, 0.77 g of a white solid compound of the formula (5) was obtained. yield: 90%.

EXAMPLE 1

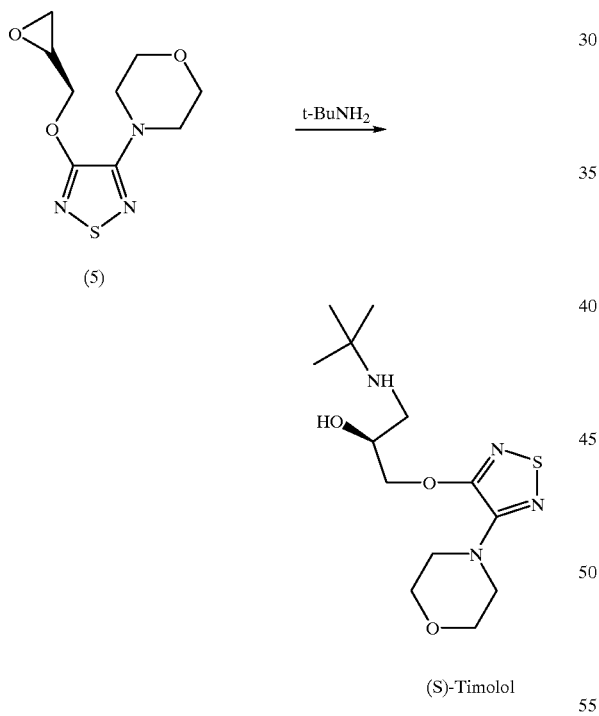

The formula (5) compound (0.15 g), t-butylamine (7 ml), and H$_2$O (0.25 ml) were added into a 10 ml flask. The solution was heated to the reflux. When the reaction was completed, ethyl acetate (20 ml) was added. After concentration and purification, 0.19 g of a white solid compound of (S)-Timolol was obtained. yield: 97%.

EXAMPLE 2

Refer to the procedure of preparation example 5, preparation example 6, and example 1, substitute the formula (3) compound with the formula (12) compound, and substitute t-BuNH$_2$ with 2-amino propane to obtain (S)-Propranolol.

From the foregoing description, one skilled in the art can easily ascertain the essential characteristics of this invention, and, without departing from the scope thereof, can make various changes and modifications of the invention to adapt it to various usages and conditions. Thus, other embodiments are also within the claims.

What is claimed is:

1. A method for preparing 3-amino-1,2-propandiol derivatives of the formula (I)

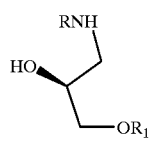

(I)

wherein:

R is C$_{1-4}$ alkyl;

R$_1$ is 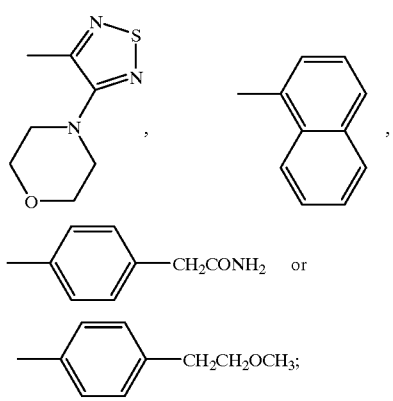

which comprises reacting a compound of the formula (II)

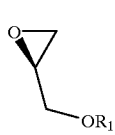

(II)

wherein R$_1$ is defined as the above with RNH$_2$, wherein R is defined as above, wherein said formula (II) compound is prepared by the following steps:

i) reacting tho formula (IV) compound,

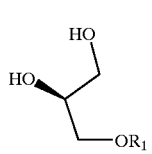

(IV)

wherein R$_1$ is defined as the above, with R$_2$SO$_2$Cl, wherein R$_2$ is C$_{1-4}$ alkyl, phenyl, benzyl, or a phenyl group substituted by $C_{1-4}$ alkyl group or halogon; and ii) treating with NaH.

2. The method of claim 1, wherein R is isopropyl or t-butyl.

3. The method of claim 1, wherein $R_1$ is

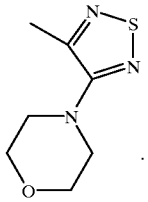

4. The method of claim 1, wherein said formula (I) is (S)-Timolol.

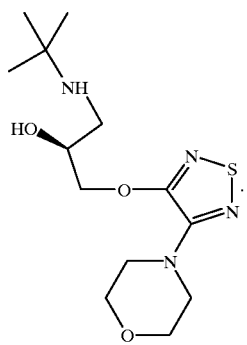

(S)-Timolol

5. The method of claim 1, wherein said formula (IV) compound is prepared by the following steps:

i) reacting the formula (VI) compound

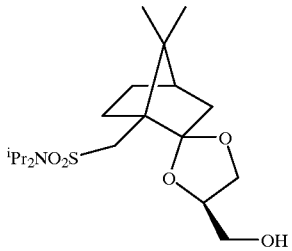

(VI)

with $R_1X$, wherein $R_1$ is defined as the above, and X is halogen; and ii) proceeding a hydrolysis reaction.

6. The method of claim 1, wherein said formula (IV) compound is prepared by the following steps:

i) reacting the formula (VI) compound with $R_2SO_2Cl$, wherein $R_2$ is defined as the above;

ii) treating with $R_1OH$, wherein $R_1$ is defined as the above; and iii) proceeding a hydrolysis reaction.

* * * * *